US009248130B2

(12) United States Patent
Scott, III

(10) Patent No.: US 9,248,130 B2
(45) Date of Patent: Feb. 2, 2016

(54) METHODS AND COMPOSITIONS FOR TREATING THYROID-RELATED MEDICAL CONDITIONS WITH REDUCED FOLATES

(71) Applicant: Linzy O. Scott, III, Atlanta, GA (US)

(72) Inventor: Linzy O. Scott, III, Atlanta, GA (US)

(*) Notice: Subject to any disclaimer, the term of this patent is extended or adjusted under 35 U.S.C. 154(b) by 0 days.

(21) Appl. No.: 14/043,309

(22) Filed: Oct. 1, 2013

(65) Prior Publication Data

US 2014/0030359 A1     Jan. 30, 2014

Related U.S. Application Data

(63) Continuation of application No. 13/687,109, filed on Nov. 28, 2012, now Pat. No. 8,575,171, which is a continuation of application No. 12/833,933, filed on Jul. 9, 2010, now Pat. No. 8,343,974.

(60) Provisional application No. 61/270,741, filed on Jul. 13, 2009, provisional application No. 61/270,615, filed on Jul. 10, 2009.

(51) Int. Cl.

| A61K 31/519 | (2006.01) |
|---|---|
| A61K 31/593 | (2006.01) |
| A61K 31/714 | (2006.01) |
| A61K 33/06 | (2006.01) |
| A61K 33/26 | (2006.01) |
| A61K 45/06 | (2006.01) |
| A61K 31/59 | (2006.01) |
| A61K 31/7056 | (2006.01) |
| A61K 31/205 | (2006.01) |

(52) U.S. Cl.
CPC ............. *A61K 31/519* (2013.01); *A61K 31/205* (2013.01); *A61K 31/59* (2013.01); *A61K 31/593* (2013.01); *A61K 31/7056* (2013.01); *A61K 31/714* (2013.01); *A61K 33/06* (2013.01); *A61K 33/26* (2013.01); *A61K 45/06* (2013.01)

(58) Field of Classification Search
CPC combination set(s) only.
See application file for complete search history.

(56) References Cited

U.S. PATENT DOCUMENTS

| 4,205,126 | A | 5/1980 | Cartaya |
|---|---|---|---|
| 5,059,595 | A | 10/1991 | Le Grazie |
| 5,316,938 | A | 5/1994 | Keen et al. |
| 5,538,734 | A | 7/1996 | Le Grazie |
| 5,563,126 | A | 10/1996 | Allen et al. |
| 5,591,709 | A | 1/1997 | Lindenbaum |
| 5,633,162 | A | 5/1997 | Keen et al. |
| 5,681,561 | A | 10/1997 | Hirshowitz et al. |
| 5,795,873 | A | 8/1998 | Allen |
| 5,997,915 | A | 12/1999 | Bailey et al. |
| 6,011,040 | A | 1/2000 | Muller et al. |
| 6,090,567 | A | 7/2000 | Jakobovits et al. |
| 6,153,582 | A | 11/2000 | Skelnik |
| 6,207,651 | B1 | 3/2001 | Allen et al. |
| 6,248,363 | B1 | 6/2001 | Patel et al. |
| 6,254,904 | B1 | 7/2001 | Bailey |
| 6,271,374 | B1 | 8/2001 | Muller et al. |
| 6,297,224 | B1 | 10/2001 | Allen et al. |
| 6,309,663 | B1 | 10/2001 | Patel et al. |
| 6,441,168 | B1 | 8/2002 | Muller et al. |
| 6,451,360 | B2 | 9/2002 | Bailey et al. |
| 6,528,496 | B1 | 3/2003 | Allen et al. |
| 6,673,381 | B2 | 1/2004 | Bailey et al. |
| 6,720,001 | B2 | 4/2004 | Chen et al. |
| 6,750,005 | B2 | 6/2004 | Leif et al. |
| 6,808,725 | B2 | 10/2004 | Bailey et al. |
| 7,074,426 | B2 | 7/2006 | Kochinke |
| 7,172,778 | B2 | 2/2007 | Bailey et al. |
| RE39,792 | E | 8/2007 | Keen et al. |
| 7,354,590 | B2 | 4/2008 | Shastri et al. |
| 7,517,342 | B2 | 4/2009 | Scott et al. |
| 7,598,031 | B2 | 10/2009 | Liew |
| 7,662,378 | B2 | 2/2010 | Goldenberg et al. |
| 7,662,558 | B2 | 2/2010 | Liew |
| 7,674,490 | B2 | 3/2010 | Bailey et al. |
| 7,682,606 | B2 | 3/2010 | Shastri et al. |

(Continued)

FOREIGN PATENT DOCUMENTS

| EP | 1949906 | 7/2008 |
|---|---|---|
| EP | 2311448 | 4/2011 |

(Continued)

OTHER PUBLICATIONS

Zheng et al., Toxicological Sciences 61: 107-114 (2001).*

(Continued)

*Primary Examiner* — Robert A Wax
*Assistant Examiner* — Thor Nielsen
(74) *Attorney, Agent, or Firm* — Meunier Carlin & Curfman LLC

(57) ABSTRACT

The present invention provides methods and compositions for treating thyroid-related medical conditions. Many thyroid-related medical conditions exist that go undiagnosed and untreated. These conditions may be prevented and treated with reduced folates and vitamin B12. Administration of reduced folates and vitamin B12 will prevent or treat cerebrospinal folate deficiency, which is linked to thyroid-related medical conditions. Administration of reduced folates and vitamin B12 will also prevent or treat conditions associated with masked megaloblastic anemia and hypothyroidism, and other conditions brought upon through improper thyroid function. Additionally, it is commonplace to treat many thyroid conditions with anti-thyroid drugs or thyroid stimulating drugs. This practice alone is also responsible for causing, or not beneficially addressing, adverse conditions that can be prevented or treated through the methods and compositions discussed herein.

4 Claims, No Drawings

(56) References Cited

U.S. PATENT DOCUMENTS

| | | | |
|---|---|---|---|
| RE41,974 | E | 11/2010 | Keen et al. |
| 7,838,524 | B2 | 11/2010 | Lee et al. |
| 8,343,974 | B2 | 1/2013 | Scott, III |
| 2001/0049352 | A1 | 12/2001 | Mark et al. |
| 2002/0042096 | A1 | 4/2002 | Rosen et al. |
| 2002/0193318 | A1 | 12/2002 | Burke et al. |
| 2003/0012826 | A1 | 1/2003 | Giordano et al. |
| 2003/0077254 | A1 | 4/2003 | Ramaekers |
| 2003/0077602 | A1 | 4/2003 | Rosen et al. |
| 2003/0198668 | A1 | 10/2003 | Franz et al. |
| 2003/0233035 | A1 | 12/2003 | Rubenstein |
| 2004/0023961 | A1 | 2/2004 | Dumas et al. |
| 2004/0202719 | A1 | 10/2004 | Zion et al. |
| 2004/0258711 | A1 | 12/2004 | Shastri et al. |
| 2005/0031544 | A1 | 2/2005 | Njemanze |
| 2005/0031651 | A1 | 2/2005 | Gervais et al. |
| 2005/0143340 | A1 | 6/2005 | Collins |
| 2006/0134109 | A1 | 6/2006 | Gaitanaris et al. |
| 2006/0252049 | A1 | 11/2006 | Shuler et al. |
| 2007/0093462 | A1 | 4/2007 | Rogers et al. |
| 2007/0243132 | A1 | 10/2007 | Russell-Jones et al. |
| 2008/0066741 | A1 | 3/2008 | LeMahieu et al. |
| 2008/0220441 | A1 | 9/2008 | Birnbaum et al. |
| 2008/0292596 | A1 | 11/2008 | Shastri et al. |
| 2009/0088404 | A1 | 4/2009 | Freedman |
| 2009/0170858 | A1 | 7/2009 | Bailey et al. |
| 2010/0061974 | A1 | 3/2010 | Quadros et al. |
| 2010/0087546 | A1 | 4/2010 | Appleton |
| 2010/0266496 | A1 | 10/2010 | Hansen et al. |
| 2010/0304418 | A1 | 12/2010 | Moussavi et al. |

FOREIGN PATENT DOCUMENTS

| | | |
|---|---|---|
| WO | 0061154 | 10/2000 |
| WO | 03068223 | 8/2003 |
| WO | 2004/092334 | 10/2004 |
| WO | 2006/124676 | 4/2006 |
| WO | 2006119589 | 11/2006 |
| WO | WO 2007002356 A2 * | 1/2007 |

OTHER PUBLICATIONS

Ormazabal et al., Clin Chim Acta 371: 159-162 (2006).*
American Society of Health System Pharmacists—Co-trimoxazole (2007).
American Society of Health System Pharmacists—Leucovorin Calcium (2007).
American Society of Health System Pharmacists—Methimazole (2007).
American Society of Health System Pharmacists—Propylthiouracil (2007).
Autoimmune Thyroid Disease, An Unfortunate and Lengthy Adventure in Misdiagnosis, Archive for Jan. 2007.
Bahn et al., The Role of Propylthiouracil in the Management of Graves' Disease in Adults: Report of a Meeting Jointly Sponsored by the American Thyroid Association and the Food and Drug Administration, Thyroid, 19(7):673-674 (2009).
Berbel et al., Role of Late Maternal Thyroid Hormones in Cerebral Cortex Development: An Experimental Model for Human Prematurity, Cerebral Cortex, 20:1462-1475 (2010).
Blehaut et al., Effect of Leucovorin (Folinic Acid) on the Developmental Quotient of Children with Down's Syndrome (Trisomy 21) and Influence of Thyroid Status, PLoS One, 5(1):e8394 (Jan. 11, 2010).
Brugnara et al., Red Blood Cells, Introduction to Anemias, Blood, Principles and Practice of Hematology, Second Edition, pp. 1345-1360 (2003).
Carmel et al., Disorders of Cobalamin and Folate Metabolism, Blood, Principles, and Practice of Hematology, Second Edition, pp. 1361-1397, 1992-1993 (2003).
Catania et al., Hypothesis: A History of Hypothyroidism or a Family History of Pernicious Anaemia are Useful in Identifying Masked Pernicious Anaemia in Elderly Patients with Microcytic Hypochromic Anaemia, Age and Ageing, 18:279-281 (1989).
Djukic, Folate-Responsive Neurologic Diseases, Pediatric Neurology, 37:387-397 (2007).
FDA Drug Safety Communication: New Boxed Warning on severe liver injury with propylthiouracil (Apr. 21, 2010).
FDA Notice—Draft Guidance for Industry on in Vivo Pharmacokinetics and Bioavailability Studies and in Vitro Dissolution Testing for Levothyroxine Sodium Tablets; Availability (Jun. 10, 1999).
Hashimotos—Super Down Syndrome, http://sites.google.com/site/superdownsyndrome/thyroid/hashimotos.
Hepatic Toxicity Following Treatment for Pediatric Graves' Disease Meeting Oct. 28, 2008, Eunice Kennedy Shriver National Institute of Child Health and Human Development, Rockville, MD.
Hyland et al., Cerebral folate deficiency, J. Inherit. Metab. Dis., 33:563-570 (2010).
International Search Report and Written Opinion for PCT/US10/41631 dated Sep. 27, 2010.
Jabbar et al., Vitamin B12 deficiency common in primary hypothyroidism, J. Pak. Med. Assoc., 58(5):258-261 (2008).
Marqusee et al., The Blood in Hypothyroidism, Werner & Ingbar's the Thyroid, A Fundamental and Clinical Text, Ninth Edition, pp. 803-805 (2005).
Medical Neurogenetics, LLC summary letter issued by John M. Shoffner, M.D.
Mégarbaneé et al., The 50th anniversary of the discovery of trisomy 21: The past, present, and future of research and treatment of Down Syndrome, Genetics in Medicine, 11(9):611-616 (2009).
Momotani et al., Effects of Propylthiouracil and Methimazole on Fetal Thyroid Status in Mothers with Graves' Hyperthyroidism, J. of Clinical Endocrinology and Metabolism, 82(11):3633-3636 (1997).
Moretti et al., Cerebral folate deficiency with developmental delay, autism, and response to folinic acid, Neurology, 64:1088-1090 (2005).
Nedrebo et al., Plasma Total Homocysteine in Hyper- and Hypothyroid Patients Before and During 12 Months of Treatment, Clinical Chemistry, 47(9):1738-1741 (2001).
Neilan et al., Response of Motor Complications in Cockayne Syndrome to Carbidopa-Levodopa, Arch. Neurol., 65 (8):1117-1121 (2008).
Parravicini et al., Neonatal Leukocyte Physiology and Disorders, Avery's Diseases of the Newborn, Eighth Edition, Edited by H. William Taeusch et al., pp. 1215-1225, 1593 (2005).
Reuss et al., The Relation of Transient Hypothyroxinemia in Preterm Infants to Neurologic Development at Two Years of Age, New England J. Med., 334(13):821-827 (1996).
Rivkees et al., AACE Patient Safety, Editorials, Propylthiouracil (PTU) Hepatotoxicity and Graves' Disease Therapy (2009).
Rodreíguez-Salinas et al., Malnutrition and Neurologic Disorders: A Global Overview, World Federation of Neurology, Seminars in Clinical Neurology, Neurologic Consequences of Malnutrition, 6:1-17, 28 (2008).
Schwartz, Autoimmune Folate Deficiency and the Rise and Fall of "Horror Autotoxicus," New England J. Med., 352 (19):1948-1950 (2005).
Spivak, The blood in systemic disorders, Lancet, 355:1707-1712 (2000).
Spivak, Masked Megaloblastic Anemia, Arch. Intern. Med., 142:2111-2114 (1982).
Van Staa et al., The risk of neutropenia is higher for antithyroid drugs than many other classes of drugs, Clinical Thyroidology, XV(2)25 (2003).
Stagnaro-Green et al., Guidelines of the American Thyroid Association for the Diagnosis and Management of Thyroid Disease During Pregnancy and Postpartum, Thyroid, 21(10):1-45 (2011).
Strauss, Granulopoiesis and Neutrophil Function in the Neonate, Developmental and Neonatal Hematology, Edited by James A. Stockman et al., pp. 87-101 (1988).
Streetman et al., Diagnosis and Treatment of Graves Disease, Endocrinology, 37(7-8):1100-1109 (2003).

(56) References Cited

OTHER PUBLICATIONS

Streuli et al., Macrocytic Anaemia with Folic Acid Deficiency in Hypothyroidism, Dtsch. Med. Wochenschr., 103 (22):936-939 (1978) (abstract).
Tajiri et al., Hepatic Dysfunction in Primary Hypothyroidism, Endocrinol. Jpn., 31(1):83-91 (1984) (abstract).
Werner, Megaloblastic anemia and disorders of cobalamin and folate metabolism, Pediatric Hematology, Third Edition, Edited by Robert J. Arceci et al., pp. 105-129 (2006).
www.pamlab.com excerpt on CerefolinNAC®, accessed Apr. 13, 2011.
www.pamlab.com excerpt on Deplin®, accessed Apr. 13, 2011.
www.pamlab.com excerpt on Foltx®, accessed Apr. 13, 2011.
www.pamlab.com excerpt on Metanx®, accessed May 2, 2011.
www.pamlab.com excerpt on Néevo® and NéevoDHA®, accessed May 2, 2011.
www.sjpharma.com excerpt on Cardiotek®-Rx, accessed May 2, 2011.
FDA Alert—Information for Healthcare Professionals—Propylthiouracil-Induced Liver Failure (Jun. 4, 2009).
Benvenga et al., Effects of Carnitine on Thyroid Hormone Action, Ann. N.Y. Acad. Sci., 1033:158-167 (2004).
Sinclair et al., Muscle Carnitine in Hypo- and Hyperthyroidism, Muscle & Nerve, 32:357-359 (2005).
Examination Report for NZ Application No. 598171 dated Oct. 2, 2012.
Extended European Search Report for Application No. 10797960.1 dated Nov. 19, 2012.
Written Opinion for SG Application No. 201200206-9 dated Jan. 30, 2013.
Martin, Increased folic acid requirements resulting from thyroxin injection, Am. J. Digestive Diseases, 14 (11):341-342 (1947).
Rezvanian et al., The effect of folic acid and levothyroxine combination therapy on serum homocysteine levels of hypothyroid patients, Iranian J. Endocrinol. Metabol., 7(4):315-319 (2006).
Hines et al., Megaloblastic anemia secondary to folate deficiency associated with hypothyroidism, Ann. Inter. Med., 68(4):792-805 (1968).
D'Adamo, Methylenetetrahydrofolate reductase (MTHFR) polymorphism, http://www.drpeterjdadamo.com/wiki/wiki.pl/Methylenetetrahydrofolate_reductase_(MTHFR)_polymorphism, May 26, 2006, accessed Nov. 8, 2012.
Bowthorpe, Ferritin and hypothyroid, http://web.archive.org/web120090620035205/http://www.stopthethyroidmadness.com/ferritin, Jun. 20, 2009, accessed Nov. 7, 2012.
Support for underactive thyroid gland, http://web.archive.org/web/20090531174357/http://www.health4youonline.com/article_underactive_thyroid.htm, May 31, 2009, accessed Nov. 7, 2012.
Pattou et al., Hypocalcemia following thyroid surgery: incidence and prediction of outcome, World J. of Surgery, 22 (7):718-724 (1998).
Office Action from CN201080040828.X dated Jan. 31, 2013.
Benvenga et al., Usefulness of l-carnitine, a naturally occurring peripheral antagonist of thyroid hormone action, in iatrogenic hyperthyroidism: A randomized, double-bind, placebo-controlled clinical trial, J. Clin. Endocr. Metabol., 86 (8):3579-3594 (2001).
Benvenga et al., Carnitine is a naturally occurring inhibitor of thyroid hormone nuclear uptake, Thyroid, 10 (12):1043-1050 (2000).
Kumar, Altered maternal thyroid function: effect of l-carnitine supplementation on fetal and neonatal myocardial free fatty acid oxidation, in vitro, Indian J. Clinc. Biochem., 13(2):87-91 (1998).
Vreugdenhil et al., Anaemia in rheumatoid arthritis: the role of iron, vitamin B12, and folic acid deficiency, and erythropoietin responsiveness, Annals of Rheumatic Disease, 49:93-98 (1990).
Maeda et al., Hypoparathyroidism and pseudohypoparathyroidism, Arq. Bras. Endocrinol. Metab., 50(4):664-673 (2006).
Xin et al., Cost-effectiveness analysis of popularizing results of preventing neural tube defects (NTDs) of women by uses of folic acid, Chinese J. Med. Sci. Res. Manag., 14(2):90-92 (2001).

Guangxia et al., Changes in blood plasma tHcy and serum folic acid, vitamin B12, and cholesterol regarding primary hypothyroidism, Shanxi Clinical Med. J., 10(8):569-570 (2001) (English abstract).
Jin, Nutritional anemia, Chinese J. Practical Inter. Med., 29(7):588-592 (2009) (English abstract).
Qingwu, One case of pancytopenia of a patient with hyperthyroidism caused by use of methimazole, Clinical Focus, 19(2):108 (2004) (Translation).
Shaojun, Analysis of diagnosis of 33 elderly hypothyroids with coronary heart diseases, China Foreign Med. Treat., 11:21 (2008) (English abstract).
Xin et al., Cost-effectiveness analysis of popularizing results of preventing neural tube defects (NTDs) of women by uses of folic acid, Chinese J. Med. Sci. Res. Manag., 14(2):90-92 (2001) (English abstract).
Hyperthyroidism accessed at http://www.merckmanuals.com/home/hormonal_and_metabolic_disorders/thyroid_gland_disorders/hyperthyroidism.html#v771993 on May 17, 2013.
Examination Report for AU Application No. 2010271178 dated Oct. 1, 2014.
Office Action for CN Application No. 201080040828.X dated May 30, 2014 (English Translation).
Office Action for CN Application No. 201080040828.X dated Oct. 16, 2013 (English Translation).
Office Action for EA Application No. 201270160, dated Aug. 6, 2014 (English Translation).
Examination Report for EP 10797960.1, dated Sep. 6, 2013.
Office Action for IL Application No. 217401 dated Apr. 27, 2014 (English Translation).
Office Action for MX Application No. MX/a/2012/000535 dated Sep. 30, 2014 (English Translation).
Office Action for JP Application No. 2012-519794 dated Jul. 25, 2014 (English translation).
Office Action for MX Application No. MX/a/2012/000535 dated Feb. 25, 2014 (English translation).
Examination Report for NZ Application No. 598171 dated Oct. 6, 2014.
Examination Report for NZ Application No. 598171 dated Mar. 18, 2014.
Examination Report for NZ Application No. 622518 dated Mar. 18, 2014.
Examination Report for SG Application No. 201200206-9 dated Oct. 18, 2013 (English Translation).
Office Action for UA Application No. 201201434 dated Oct. 2, 2013 (English Translation).
Decision to Grant for UA Application No. 201201434 dated Sep. 30, 2014 (English Translation).
Office Action for AP Application No. AP/P/2012/006124 dated Jul. 4, 2014.
"Ferritin and hypothyroid," Wordpress, 2005, 4 pages.
Hajigholami, R.H., et al., "The effect of folic acid and levothyroxine combination therapy on serum homocysteine levels of hypothyroid patients," Caspian Journal of Internal Medicine, 2012, vol. 3, Issue 3, pp. 504-505.
Lindenbaum, J., et al., "Folic acid clearances and basal serum folate levels in patients with thyroid disease," Journal of Clinical Pathology, vol. 17, 1964, pp. 666-670.
Mischoulon, D., et al., "The Role of Folate in Depression and Dementia," Journal of Clinical Psychiatry, vol. 68, Jan. 18, 2007, pp. 28-33.
Özmen, B., et al., "Impact of Renal Function or Folate Status on Altered Plasma Homocysteine Levels in Hypothyroidism," Endocrine Journal, vol. 53, No. 1, 2006, pp. 119-124.
Viswanathan, G., et al., "Altered metabolism of folates and lipids in hyperthyroid and hypothyroid rats," Indian Journal of Biochemistry & Biophysics, vol. 33, 1996, pp. 311-314.
Pasquali, et al., "Effects of Thyroxine on the Synthesis of Folate Coenzymes in Rat Liver," Biochemical Journal, 1970, 116:217-221.
Orzechowska-Pawilojc et al., "Homocysteine, Folate and Cobalamin Levels in Hypothyroid Women Before and After Treatment," Endocrine Journal, 2007, 54(3):471-476.

(56) References Cited

OTHER PUBLICATIONS

Obeid et al., "Biomarkers of Folate and Vitamin B12 are Related in Blood and Cerebrospinal Fluid," Clinical Chemistry, 2007, 53(2):326-333.
Sjoberg et al., "L-Thyroxine Treatment and Neurotransmitter Levels in the Cerebrospinal Fluid of Hypothyroid Patients: A Pilot Study," European Journal of Endocrinology, 1998, 139:493-497.
Kaufman, "Some Metabolic Relationships Between Biopterin and Folate: Implications for the 'Methyl Trap Hypothesis'," Neurochemical Research, 1991, 16(9):1031-1036.
Blau et al., "Tetrahydrobiopterin Deficiencies Without Hyperphenylalaninemia: Diagnosis and Genetics of DOPA-responsive Dystonia and Sepiapterin Reductase Deficiency," Molecular Genetics and Metabolism, 2001, 74(1-2):172-185.
Haavik et al., "Recombinant Human Tyrosine Hydroxylase Isozxymes Reconstitution with Iron and Inhibitory Effect of Other Metal Ions," European Journal of Biochemistry, 1991, 199:371-378.
Papakostas et al., "L-methylfolate as Adjunctive Therapy for SSRI-Resistant Major Depression: Results of Two Randomized, Double-Blind, Parallel-Sequential Trials," American Journal of Psychiatry, 2012, 169(12):1267-1274.

Orzechowska-Pawilojc et al., "Homocysteine, folate, and cobalamin levels in hyperthyroid women before and after treatment," Polish Journal of Endocrinology, 2009, 60(6):443-448.
Neil, N., et al., "Treatment Study of Methylation Cycle Support in Patients with Chronic Fatigue Syndrome and Fibromyalgia," 9th International IACFS/ME Conference, Mar. 12-15, 2009.
Abalovich, M., et al., "Management of Thyroid Dysfunction During Pregnancy and Postpartum: An Endocrine Society Clinical Practice Guideline," Journal of Clinical Endocrinology & Metabolism 92(8):S1-547, 2007.
Royal College of Physicians, "The Diagnosis and Management of Primary Hypothyroidism," dated Nov. 19, 2008, at: http://www.british-thyroid-association.org/news/Docs/hypothyroidism_statement.pdf.
Jonklaas, J., et al. "Guidelines for the Treatment of Hypothyroidism," Thyroid 24(12):1670-1751, 2014.
Official Action in Mexican application MX/a/2012/000535 dated Apr. 23, 2015.
Official Action in Israeli application 217401 dated Jul. 16, 2015.
Official Action in Philippines application 1-2012500063 dated Jul. 22, 2015.
Official Action in Japanese application 2012-519794 dated Jul. 30, 2015.

* cited by examiner

METHODS AND COMPOSITIONS FOR TREATING THYROID-RELATED MEDICAL CONDITIONS WITH REDUCED FOLATES

CROSS REFERENCE TO RELATED APPLICATIONS

This application is a continuation of U.S. application Ser. No. 13/687,109 filed on Nov. 28, 2012, whose status is allowed, and which is a continuation of U.S. application Ser. No. 12/833,933, filed on Jul. 9, 2010, issued as U.S. Pat. No. 8,343,974 on Jan. 1, 2013, and which claims the benefit of priority to U.S. Provisional Application No. 61/270,615 filed on Jul. 10, 2009 and U.S. Provisional Application No. 61/270,741 filed on Jul. 13, 2009, which are each incorporated by reference herein in their entireties.

BACKGROUND

Developmental problems associated with folic acid deficiency are well known in the art. Perhaps neural tube defects in fetuses are the most common problem associated with folate deficiency. Expecting mothers are routinely placed on a folic acid regimen. Additionally, nursing mothers are also supplemented with folic acid to continue to provide nutrition to the newborn. During the prenatal and perinatal periods, folate is essential for adequate enclosure of the neural tube by dermal tissues. In recent studies, it has been shown that women with increased levels of plasma homocysteine and decreased levels of erythrocyte folate have a greater risk of having an offspring with a neural tube defect. It is believed that during the early stages of pregnancy (prior to the development of the placenta) transport of folates to the fetus is primarily performed by the maternal erythrocytes. Inadequate folate levels in maternal erythrocytes are a significant factor in the lack of progression of neural tube closure in utero.

Folate helps produce and maintain new cells; this is critically important in cells with rapid growth that undergo frequent cell division such as in infancy and pregnancy. Folate is needed to form DNA and RNA, and both adults and children need folate to make normal red blood cells. It is essential that folates are part of the daily nutritional consumption for adequate human health.

Folates also play a critical role in the reduction of plasma homocysteine levels. An increased amount of homocysteine in the plasma has been associated with heart disease. Folates have been shown to reduce the calcification of plaques during an acute ischemic attack; thereby reducing the long-term effects of cardiovascular disease. Thus, folates are major components of cardiovascular functionality.

Folate is an essential water-soluble B. vitamin that occurs naturally in food. As a result of these important metabolic activities, several dietary derivatives of folate are manufactured as supplements. Although most of the derivatives are capable of becoming converted into the metabolically active form (6S)5-methyltetrahydrofolate, the enzyme kinetics of such conversion can differ dramatically as well as the absorption rate and it is these differences that are important in determining the hierarchy of performance.

Folates are a group of pteroyglutamate acids that become structurally and functionally altered when reduced (adding electrons) or oxidized (removing electrons). In humans, folates are absorbed most readily as 5-methyltetrahydrofolate and it is the principal circulating form of folate. Other derivatives are hydrolyzed in the intestinal jejunum and the liver to the active form with an intermediate stable form (5,10-methylenetetrahydrofolate).

5-methyltetrahydrofolate is the predominant form of folate in the circulatory system and is the type of folate that can cross the blood-brain barrier. 5-methyltetrahydrofolate is critical for brain development and normal mental health.

The endocrine system is a system of glands, each of which secretes a type of hormone into the bloodstream to regulate the body. The endocrine system is an information signal system like the nervous system. Hormones regulate many functions of an organism, including mood, growth and development, tissue function, and metabolism.

Thyroid-related medical conditions, and medications that are used in connection with thyroid conditions, are known to cause hematological issues in individuals, as well as in fetuses of such individuals who may be pregnant, or the children who receive breast milk from such individuals who have thyroid-related medical conditions and/or who are on thyroid medication. In addition, these thyroid-related medical conditions, and the medications that are used in connection with thyroid conditions, are known to cause adverse hepatic conditions regarding the liver, as well as having an adverse impact on other organs. Moreover, in addition to those persons who have thyroid-related medical conditions or who are taking medications for thyroid conditions, environmental conditions, and environmental contaminants are also known to impact the thyroid system of an individual, as well as the fetus of such individual or child nursing from such individual. Thus, the thyroid system can be impacted by thyroid-related medical conditions that develop within one's own body, by certain medications, and by the environment.

Typically, thyroid conditions are treated with medication to address the thyroid condition and bring the patient to a euthyroid state. That is the focus of the medical community and pharmaceutical community. However, bringing an individual to a euthyroid state does not sufficiently address the adverse conditions associated with low folate, as well as vitamin B12, and specifically low cerebrospinal folate. The medical and pharmaceutical communities have not been able to sufficiently address the further complications the thyroid-related medical conditions, and/or the medications that are used in connection with thyroid conditions, cause. For instance, anti-thyroid drugs are known to cause (a) numerous blood disorders (including, but not limited to, megaloblastic anemia, pancytopenia, aplastic anemia, neutropenia, agranulocytosis, thrombocytopenia, and leukopenia), (b) bone marrow suppression, and (c) hepatic dysfunction. In addition, thyroid-related medical conditions are known to cause similar conditions. For instance, hypothyroidism is known to cause iron, folate and/or vitamin B12 deficiencies, which with respect to folate or vitamin B12 deficiencies, can cause "macrocytic" or "megaloblastic" hematological conditions leading, in some cases, to bone marrow suppression and hepatic dysfunction, as well as dysfunction in other organs (polyglandular failure syndrome for instance).

Even further, autoimmune conditions like chronic autoimmune thyroiditis and Hashimoto's thyroiditis associated with pernicious anemia can cause even further vitamin B12 deficiencies that will not be corrected solely by thyroid hormone replacement, but also require specific vitamin B12 supplementation. Moreover, additional conditions that complicate the clinical picture are (1) "masked megaloblastic anemia" conditions that can arise from simultaneous iron and folate/vitamin B12 deficiencies, (2) lack of vitamin B12 which is critical in the metabolic pathway of converting folate into its biologically useful form, and (3) "polymorphisms" that are commonplace. For instance, the methylenetetrahydrofolate (MTHFR) polymorphism is very common, by some accounts up to 40% of the U.S. population. As a result, some individuals are naturally more susceptible to having cerebrospinal folate issues, or ancillary folate and/or vitamin B12 issues, than others based on whether or not they have the polymorphism. Yet, notwithstanding the foregoing, thyroid-related medical conditions and drugs that are used to treat thyroid conditions are not augmented with suitable folate and B12 supplementation protocols sufficient to prevent or ameliorate the adverse effects of low cerebrospinal folate.

FIELD OF INVENTION

This invention is generally in the field of treating thyroid conditions with a folate and vitamin B12. Folate is a critical vitamin that is required for proper nutrition. Folate is important in forming DNA and RNA, therefore it is critical in cells that are growing or undergo frequent cell division. Folate deficiencies have led to harmful and serious health conditions in children as well as in adults. As a result, folate is especially important for pregnant mothers, nursing mothers and newborns.

What has previously been unknown, or at least underappreciated, is the relationship between the thyroid and levels of folate, as well as vitamin B12, in the blood. Hypothyroid individuals have been found to suffer folate, as well as, vitamin B12 deficiencies; and as such, they are prone to the other problems that are also associated with low folate levels. It is now discovered that conditions of hypothyroidism have led to folate deficiencies in cerebrospinal fluid. There has been a newly discovered case involving the treatment of hyperthyroidism that has also led to folate deficiencies in cerebrospinal fluid. This is because the drugs that are taken to treat hyperthyroidism suppress the thyroid and in some cases have suppressed it to the extent that it leads to hypothyroidism and folate deficiencies in cerebrospinal fluid. In addition, these anti-thyroid drugs can cause adverse hematological and hepatic conditions that can also contribute to deficiencies in folate, as well as vitamin B12, leading to cerebrospinal folate deficiency.

This surprising discovery has led to the present invention. Providing individuals, who have had or are at risk of having thyroid-related medical conditions, with folate and vitamin B12 has shown to beneficially address and alleviate adverse outcomes associated with low folate in cerebrospinal fluid. The present invention also addresses those who must take anti-thyroid drugs or thyroid stimulating drugs or hormones. Supplementation with folates and vitamin B12 along with either anti-thyroid drugs or thyroid stimulating drugs can provide a better means of preventing and/or treating folate deficiencies and the associated problems from such deficiencies.

This invention will help prevent and further help diagnose the cause of folate deficiencies in some individuals, as thyroid-related medical conditions are presently not part of the focus of the medical and pharmaceutical communities. Further, leading researchers in the field of cerebrospinal folate deficiency have mainly focused on antibodies attacking the folate receptor or mitochondrial defects as the cause of cerebrospinal folate deficiency.

There is clearly a need to make the relationship between thyroid function and folate deficiencies in cerebrospinal fluid known so that it may be prevented and treated. This invention addresses that need.

SUMMARY OF THE INVENTION

The present invention provides methods and compositions for preventing and/or treating people with thyroid-related medical conditions from developing problems associated with folate deficiencies. In some embodiments, the present invention provides a method of administering folate to people with thyroid-related medical conditions. In some embodiments, the present invention provides a method of administering folate and vitamin B12 to people with thyroid-related medical conditions. In some embodiments, the present invention further provides a method of administering a reduced folate to people with thyroid-related medical conditions. In some embodiments, the present invention further provides a method of administering a reduced folate and vitamin B12 to people with thyroid-related medical conditions. Yet in another embodiment, the present invention further provides a method of administering folinic acid and vitamin B12 to people with thyroid-related medical conditions. And in some embodiments the administration of folate and vitamin B12 will treat or prevent cerebrospinal folate deficiency, masked megaloblastic anemia, other macrocytic anemias (which include anemias that may be masked macrocytic anemias), or hepatic dysfunction. In some embodiments, the present invention will include the administration of folate and vitamin B12 and will be coupled with the administration of iron. Other embodiments will include the administration of L-carnitine and/or calcium and/or vitamin D along with the administration of folate and vitamin B12. With respect to calcium and vitamin D, these are preferred embodiments that also address parathyroid hormone deficiencies.

In some embodiments, the present invention provides a method of administering folate and vitamin B12 to people with hypothyroidism or hyperthyroidism. In other embodiments, the present invention provides a method of administering folate and vitamin B12 to people that have been treated with radioactive iodine, or who have had surgery on or related to their thyroid, or who have had any procedure that has reduced the size or activity of their thyroid gland. In another embodiment, the present invention provides a method of administering folate and vitamin B12 to an individual having hypothyroxinemia or another temporary period of hypothyroidism. In yet another embodiment, the present invention provides a method of administering folate and vitamin B12 to an individual that is a fetus or nursing child of a mother or caregiver who has a thyroid-related medical condition.

In some embodiments, the present invention provides a composition of a thyroid stimulating drug, a folate, and vitamin B12. This embodiment will facilitate prevention and treatment of folate deficiencies for persons that have hypothyroidism. In other embodiments, the composition will additionally include iron, and/or L-carnitine, and/or calcium, and/ or vitamin D. In another embodiment, the present invention provides a composition of an anti-thyroid drug, a folate, and vitamin B12. This embodiment will facilitate prevention and treatment of folate deficiencies for persons that are being treated for hyperthyroidism and may also be complemented by iron, and/or L-carnitine, and/or calcium, and/or vitamin D.

In a preferred embodiment of the invention, the methods and compositions for prevention and treatment of thyroid-related medical conditions will require 5-methyltetrahydrofolic acid, or another reduced folate, and vitamin B12. In another preferred embodiment of the invention, the composition for prevention and treatment of thyroid-related medical conditions will require 5-methyltetrahydrofolic acid, or another reduced folate, and vitamin B12 with either an anti-thyroid drug or a thyroid stimulating drug. In another preferred embodiment, the composition of anti-thyroid drug or thyroid stimulating drug, folate or another reduced folate, and vitamin B12 will also comprise iron, and/or L-carnitine, and/ or calcium, and/or vitamin D. With respect to calcium and vitamin D, these are the preferred embodiments that also address parathyroid hormone deficiencies.

DETAILED DESCRIPTION OF THE INVENTION

I. Definitions

As used herein, "folate(s)" are a group of pteroyglutamate acids that become structurally and functionally altered when reduced. The term "folate" refers to folic acid and any derivatives thereof.

Folic acid, (N-[4-(2-Amino-3,4-dihydro-4-oxo-6-pteridinylmethylamino)-benzoyl]-L-glutamic acid) also known as vitamin B9 or folicin as well as N-pteroyl-L-glutamic acid and N-pteroyl-L-glutamate, is a non-reduced folate.

In humans, folates are absorbed most readily as the most active form 6(R,S)-5-methyltetrahydrofolate (6(S)-5-methyltetrahydrofolate being the most biologically active) and it is the principal circulating form of folate (referred to herein as "reduced folate"). A nonexclusive list of other reduced folates (also included in the definition of "reduced folates") are 10-methylenetetrahydrofolate, 10-formyltetrahydrofolic acid, 5-formyltetrahydrofolic acid, 5-forminino tetrahydrofolic acid, 5,10-methenyltetrahydrofolic acid, 5,10-methyltetrahydrofolic acid, L-methylfolate, and 6(R,S)-5-formyltetrahydrofolate (folinic acid), and tetrahydrofolic acid/tetrahydrofolate.

The term of "folate" as referenced herein, is used as a genus, and generally refers to any of these forms of folate: folic acid, any form of reduced folates, and 5-methyltetrahydrofolic acid.

Vitamin B12, also called cobalamin, is a water soluble vitamin. Vitamin B12 refers to a group of cobalt-containing vitamer compounds known as cobalamins: these include cyanocobalamin, hydroxocobalamin, and the two naturally occurring cofactor forms of B12 in the human body: 5'-deoxyadenosylcobalamin (adenosylcobalamin—AdoB12), the cofactor of Methylmalonyl Coenzyme A mutase (MUT), and methylcobalamin ($MeB_{12}$), the cofactor of 5-methyltetrahydrofolate-homocysteine methyltransferase (MTR).

The term "cerebrospinal folate deficiency" (also referred to as cerebral folate deficiency) is associated with low levels of 5-methyltetrahydrofolate in the cerebrospinal fluid (CSF). In some conditions, the low levels of folate in CSF is also associated with normal folate levels in the plasma and red blood cells. The onset of symptoms caused by the deficiency of folates in the brain generally begin within the first year of life, but in the examples contained herein exhibited themselves at birth or within the immediate months thereafter. This is followed by delayed development, with deceleration of head growth, hypotonia, and ataxia, followed in many cases by dyskinesias (choreo-athetosis, hemiballismus), spasticity, and speech difficulties, as well as numerous other cognitive, social, behavioral, psychological and physical conditions.

The term "masked megaloblastic anemia" is characterized by folate and/or vitamin B12 deficiencies occurring simultaneously with an iron deficiency, such that the iron deficiency masks the red blood cell indices changes of megaloblastic anemia.

The term "masked macrocytic anemias" refers to conditions where a macrocytic anemia is masked, and includes (a) masked megaloblastic anemia, (b) when a macrocytic anemia is masked by a microcytic to normocytic anemia that occurs simultaneously with the macrocytic anemia, or (c) neutropenia that is masked at birth, in part, by a phenomena whereby neutrophil counts and white blood cell values rise immediately after birth.

The term "hypothyroxinemia" refers to conditions associated with the presence of an abnormally low concentration of thyroxine in the blood.

The term "iron" as it relates to nutritional supplementation, refers to any form of iron that is generally known to supplement nutrition; for example, an iron (II) salt, an iron (III) salt, or carbonyl iron.

The term "anti-thyroid drug" is a drug, agent or medication directed against the thyroid gland for the purposes of reducing thyroid function. The anti-thyroid drugs include, but are not limited to, carbimazole, methimazole, potassium perchlorate, and propylthiouracil (PTU). These drugs are used to treat hyperthyroidism (overactivity of the thyroid gland) in order to reduce the excessive thyroid activity before surgery and to treat and maintain patients not having surgery.

The term "thyroid stimulating drug" is a drug, agent, medication or hormone that acts as a replacement for a hormone that is normally produced by the thyroid gland to regulate the body's energy and metabolism. These drugs are used for the purpose of increasing thyroid function. thyroid stimulating drugs include but are not limited to: Levothyroxine, Levothyroxine Sodium, Liothyronine Sodium, Liotrix, Thyroglobulin, Thyroid, Thyroxine, Triiodothyronine Levoxyl, Synthroid, Levo-T, Unithroid, Levothroid, Levoxine, Levolet, Novothyrox, Triostat, Cytomel and Thyrolar.

The term "thyroid-related medical condition" refers to medical conditions that arise when the thyroid gland is not functioning properly. This could include hypothyroidism (under active thyroid function), hyperthyroidism (overactive thyroid function), anatomical disorders, and tumors (including thyroid cancer). "Thyroid-related medical conditions" also arise from and include the use of agents, drugs or medications to treat the thyroid, or from environmental toxins or environmental conditions that impact the thyroid. The term "thyroid-related medical conditions" also includes complications associated with diabetes mellitus, hypoparathyroidism and polyglandular failure syndrome brought about in connection with a thyroid gland that is not functioning properly.

II. Introduction

The present invention provides methods and compositions for prevention and treatment of thyroid-related medical conditions. The invention is based on the discovery that an improperly functioning thyroid can cause harmful conditions. Some nonexclusive examples are cerebrospinal folate deficiency and masked macrocytic anemias, and hepatic dysfunction. These conditions may be prevented or treated by the administration of folate and vitamin B12. Additionally there is a certain population of individuals who are also at risk for developing conditions that may be treated with the administration of folate and vitamin B12. Some thyroid-related medical conditions such as hypothyroidism and hyperthyroidism are treated with anti-thyroid drugs or thyroid stimulating drugs. Anti-thyroid drugs can cause harmful conditions such as macrocytic blood disorders, which may be masked macrocytic anemias, as well as hepatic dysfunction, which itself may be idiosyncratic or difficult to diagnose given its unpredictability and sudden onset. The foregoing hematological and hepatic conditions can also lead to cerebrospinal folate deficiencies. As a result, the present invention includes a composition of these drugs with the addition of folate and vitamin B12.

III. Patient Population

For purposes of this invention patients are those who have been suffering from thyroid-related medical conditions or those who are at risk of suffering thyroid-related medical conditions, which thyroid conditions or risk of thyroid conditions may be caused by a number of circumstances, including, but not limited to, biological conditions within the patient's body, agents, drugs, or medications the patient has been exposed to, or environmental exposure to toxins, or other adverse environmental conditions.

In one embodiment, the individual with a thyroid-related medical condition may suffer from hypothyroidism or hyperthyroidism. In general, hypothyroidism is a condition in which the thyroid gland does not produce enough thyroid hormone. In general, hyperthyroidism is a condition in which the thyroid gland produces too much thyroid hormone. In a preferred embodiment, the patient is taking an anti-thyroid drug or a thyroid stimulating drug. While these types of patients may be at the highest risk, other similar conditions pose a risk that may be treated by the methods and compositions of this invention. For example, those persons with a thyroid-related medical condition and suffering from a macrocytic blood condition, masked megaloblastic anemia, masked macrocytic anemia or hepatic dysfunction, and those persons exposed to agents, drugs, medications, toxins and environmental conditions that cause any of the foregoing hematological or hepatic conditions may be treated with the methods and compositions of this invention.

In another embodiment, the patient has a thyroid-related medical condition related to hypothyroxinemia.

In another embodiment, the patient may be any individual treated with radioactive iodine, or who has surgery on or related to the thyroid gland, or who undergoes any other process or procedure that alters the normal function of the thyroid.

In another embodiment, the patient may be a fetus or newborn with a mother or caregiver who has a thyroid-related medical condition.

IV. Detecting Conditions a) Thyroid

One of the key discoveries of this invention is the discovery that thyroid-related medical conditions can cause cerebrospinal folate deficiencies, and the person with the thyroid condition is susceptible to all of the harms associated with cerebrospinal folate deficiencies. In one embodiment, this invention treats persons with thyroid-related medical conditions.

b) Hypothyroidism

In another embodiment, this invention treats persons with hypothyroidism. Hypothyroidism, or an improperly functioning thyroid, specifically not producing enough thyroid hormones, can lead to a person having cerebrospinal folate deficiencies. One of the aims of this invention is to treat people with hypothyroidism.

c) Hyperthyroidism

While it has been discovered that cerebrospinal folate deficiencies are more commonly associated with hypothyroidism, persons with hyperthyroidism are also the subject of this invention because they take anti-thyroid drugs to treat their hyperthyroid conditions. These drugs have the potential to lower the production of the thyroid to levels in which folate deficiencies may occur or to cause adverse macrocytic hematological or adverse hepatic conditions leading to cerebrospinal folate deficiencies. Therefore, hyperthyroidism is a condition relevant to this invention.

d) Diabetes, Hypoparathyroidism and Polyglandular Failure Syndrome

Thyroid-related medical conditions have been known to cause or contribute to diabetes, diabetes mellitus, hypoparathyroidism and polyglandular failure syndrome. Therefore, the conditions diabetes, diabetes mellitus, hypoparathyroidism and polyglandular failure syndrome brought upon by thyroid-related medical conditions are also the subject of this invention.

e) Pregnant

Those who are pregnant and suffer from thyroid-related medical conditions are also the subject of this invention, because the thyroid conditions a pregnant mother has can cause complications for the mother, as well as with the fetus and/or newborn.

f) Fetus

Because the complications of thyroid-related medical conditions may be passed from the mother to the fetus, a fetus or newborn from a mother with a thyroid-related medical condition is also the subject of this invention.

g) Nursing Child

Because the complications of thyroid-related medical conditions may be passed through the milk of a nursing mother to the newborn, a newborn from a mother with a thyroid-related medical condition is also the subject of this invention.

h) Hypothyroxinemia

Complications arising from thyroid-related medical conditions may also arise temporarily when a person is suffering from hypothyroxinemia. Periods of hypothyroxinemia have occurred during pregnancy in the mother or in the fetus. Even though this may be only a temporary period in which the thyroid is not properly functioning, harmful results may arise during this time. Therefore, hypothyroxinemia is also the subject of this invention.

i) Anti-Thyroid Drugs

A person taking anti-thyroid drugs is also the subject of this invention. It has been discovered that at times taking an anti-thyroid drug can lower the function of the thyroid substantially enough to cause cerebrospinal folate deficiency, for which this invention addresses. In addition, such agent, drug, or medication also causes adverse hematological and hepatic conditions which can also lead to cerebrospinal folate deficiencies, for which this invention addresses.

j) Thyroid Stimulating Drugs

A person taking thyroid stimulating drugs is also the subject of this invention. As this invention addresses, hypothyroidism has been linked to cerebrospinal folate deficiency. Prior to receiving a thyroid stimulating drug, a person has for the most part already suffered from a thyroid-related medical condition. In certain cases, hypothyroidism is newly discovered in an individual and during the period in which the individual remained undiagnosed, the individual may have developed deficiencies in folate or vitamin B12 or cerebrospinal folate deficiency. In other cases, the individual may have been treated with an anti-thyroid drug for hyperthyroidism, and the drug caused the individual to develop hypothyroidism, and the individual then suffers from adverse events not only related to the anti-thyroid medication (the complications of which have already been addressed herein), but also the adverse conditions of having hypothyroidism. In yet another example, the individual has had hypothyroidism, but alternates between different degrees of hypothyroidism, such that the individual may be receiving at any given time an inadequate amount of thyroid stimulating drug, thereby still allowing the adverse complications of hypothyroidism to occur. In all of the foregoing instances, this invention will prevent or treat such individual.

k) Radioactive Iodine, Surgery, or any Other Method to Reduce the Size or Activity of the Thyroid Gland The methods of this invention are also directed to a person who has received radioactive iodine, or who has had surgery on or related to the thyroid gland, or who has had any other procedure that has reduced the size and therefore the activity of the thyroid gland.

l) Hematological Conditions

It has also been discovered that macrocytic blood conditions, including masked macrocytic anemias may be brought upon by persons with thyroid-related medical conditions. As such this invention aims to prevent or treat the conditions brought upon through folate and vitamin B12 deficiencies in persons with masked macrocytic anemias.

m) Hepatic Dysfunction

It has also been discovered that hepatic dysfunction may be brought upon by persons with thyroid-related medical conditions, and in some cases, the hepatic dysfunction may be idiosyncratic or difficult to diagnose given its unpredictability and sudden onset. As such, this invention aims to prevent or treat the conditions brought upon by folate and vitamin B12 deficiencies in persons with hepatic dysfunction.

V. Prevention Methods

While many of the uses of folate are generally well known, new conditions have been discovered that require the use of folates. It is well known in the art that folate should be used for nutritional supplementation of pregnant and nursing mothers. This is due to the fact that folate is essential for DNA and RNA replication and therefore it is necessary in growing and dividing cells, which are prevalent in nursing mothers and newborns. It is also known that folate, as well as vitamin B12, may be used to address neurological conditions, including depression. However, what was not known is that some thyroid-related medical conditions can lead to cerebrospinal folate deficiencies. Therefore, it is the subject of this invention to disclose methods and compositions of administering folate and vitamin B12 to those susceptible for developing cerebrospinal folate deficiencies and therefore prevent the harmful, adverse conditions that arise from folate deficiencies.

Some of the harmful conditions that arise from cerebrospinal folate deficiencies affect development of fetuses and newborns. However, developmental problems are not limited to fetuses and newborns, as older children, adolescents, young adults and adults can be affected as well. Some of the first symptoms associated with cerebrospinal folate deficiencies are lower IQs and cognitive dysfunction. As the condition progresses, developmental delay, psychomotor regression, seizures, mental retardation, autistic features, behavioral issues and social problems may present themselves. As conditions worsen, physical function is impaired. These are only a few of the conditions that may arise from cerebrospinal folate deficiency brought upon through thyroid-related medical conditions. The methods and compositions discussed herein will prevent and have been shown to alleviate and help correct these symptoms.

One embodiment of this invention provides a method to prevent harmful conditions that arise from thyroid-related medical conditions. This embodiment comprises administering folate and vitamin B12 to people suffering from such thyroid-related medical conditions.

Administration of the folate and vitamin B12 may be done in any manner already known in the art.

In a preferred embodiment, this invention provides a method to prevent and/or treat harmful conditions that arise from hypothyroidism. Hypothyroidism results in decreased thyroid function and decreased hormone production, which regulates the endocrine system. It has been recently and surprisingly found that hypothyroidism can lead to cerebrospinal folate deficiency and all of the problems that arise from decreased folate levels. What is of even greater concern is that many of these patients suffering with cerebrospinal folate deficiency are infants whose nervous system is still developing and lack folate at a crucial point in their development. In some cases, the damage cannot be completely undone. Since the folate is deficient at such a crucial moment in development, the adverse conditions can be severe. One embodiment of this invention is to administer folate and vitamin B12 to people with hypothyroidism. This administration of folate and vitamin B12 will help to prevent problems and conditions that arise from cerebrospinal folate deficiency.

In a preferred embodiment, a reduced folate is administered with vitamin B12 to a person with thyroid-related medical conditions. A non-exclusive list of examples of reduced folates are: 10-formyltetrahydrofolic acid, 5-formyltetrahydrofolic acid, 5-forminino tetrahydrofolic acid, 5,10-methenyltetrahydrofolic acid, and 5,10-methyltetrahydrofolic acid. In a more preferred embodiment, 5-methyl tetrahydrofolic acid is administered with vitamin B12 to persons with thyroid-related medical conditions.

The amount of folate administered by the methods and compositions of this invention will depend upon the size, age, and severity of the condition of the patient. Generally the National Institutes of Health, Office of Dietary Supplements (NIH) generally recommended dosage guidelines will suffice. This is also true for the administration of vitamin B12, iron, calcium, vitamin D, and L-carnitine. In severe cases the amounts may be increased. Dosage amounts may need to be lower than NIH generally recommended dosage guidelines in the event of preventive measures, or in the event the patient is already taking supplements containing the foregoing, or in the event the patient is a premature infant or very newborn neonate.

In one embodiment, the amount of folate to be administered by the methods and compositions of this invention should be 0.5 mg to 0.1 mg of folate per kg of weight (of the patient) per day. In other cases, higher dosages of folate at 2-3 mg/kg/day are required to normalize cerebrospinal folate levels. Yet, in other cases, where preventive measures are being taken, or when the patient is a fetus, premature newborn or term neonate, then dosage amounts may be lower than the foregoing.

In one embodiment, the amount of reduced folate to be administered by the methods and compositions of this invention should be 0.1 mg to 1.0 mg of folate per kg of weight (of the patient) per day.

In a preferred embodiment, the amount of reduced folate to be administered by the methods and compositions of this invention should be 0.5 mg to 0.1 mg of folate per kg of weight (of the patient) per day. In other cases, higher dosages of folate at 2-3 mg/kg/day are required to normalize cerebrospinal folate levels. Yet, in other cases were preventive measures are being taken, or when the patient is a fetus, premature newborn or term neonate, then dosage amounts may be lower than the foregoing.

The following tables are provided by the NIH as the recommended dietary allowance for folate and other vitamins and minerals.

TABLE 1

Adequate Intake for Folate for Infants

| Age (months) | Males and Females (μg/day) |
|---|---|
| 0 to 6 | 65 |
| 7 to 12 | 80 |

TABLE 2

Recommended Dietary Allowances for Folate for Children and Adults

| Age (years) | Males and Females (μg/day) | Pregnancy (μg/day) | Lactation (μg/day) |
|---|---|---|---|
| 1-3 | 150 | N/A | N/A |
| 4-8 | 200 | N/A | N/A |
| 9-13 | 300 | N/A | N/A |
| 14-18 | 400 | 600 | 500 |
| 19+ | 400 | 600 | 500 |

TABLE 3

Recommended Dietary Allowances (RDAs) for Vitamin B12

| Age | Male | Female | Pregnancy | Lactation |
|---|---|---|---|---|
| Birth to 6 months* | 0.4 mcg | 0.4 mcg | | |
| 7-12 months* | 0.5 mcg | 0.5 mcg | | |
| 1-3 years | 0.9 mcg | 0.9 mcg | | |
| 4-8 years | 1.2 mcg | 1.2 mcg | | |
| 9-13 years | 1.8 mcg | 1.8 mcg | | |
| 14+ years | 2.4 mcg | 2.4 mcg | 2.6 mcg | 2.8 mcg |

TABLE 4

Recommended Adequate Intake for Infants and Recommended Dietary Allowances for Iron for Infants (7 to 12 months), Children, and Adults

| Age | Males (mg/day) | Females (mg/day) | Pregnancy (mg/day) | Lactation (mg/day) |
|---|---|---|---|---|
| Infants | 0.27 | 0.27 | N/A | N/A |
| 7 to 12 months | 11 | 11 | N/A | N/A |
| 1 to 3 years | 7 | 7 | N/A | N/A |
| 4 to 8 years | 10 | 10 | N/A | N/A |
| 9 to 13 years | 8 | 8 | N/A | N/A |
| 14 to 18 years | 11 | 15 | 27 | 10 |
| 19 to 50 years | 8 | 18 | 27 | 9 |
| 51+ years | 8 | 8 | N/A | N/A |

TABLE 5

Adequate Intakes (AIs) for Calcium

| Age | Male | Female | Pregnant | Lactating |
|---|---|---|---|---|
| Birth to 6 months | 210 mg | 210 mg | | |
| 7-12 months | 270 mg | 270 mg | | |
| 1-3 years | 500 mg | 500 mg | | |
| 4-8 years | 800 mg | 800 mg | | |
| 9-13 years | 1,300 mg | 1,300 mg | | |
| 14-18 years | 1,300 mg | 1,300 mg | 1,300 mg | 1,300 mg |
| 19-50 years | 1,000 mg | 1,000 mg | 1,000 mg | 1,000 mg |
| 50+ years | 1,200 mg | 1,200 mg | | |

TABLE 6

Adequate Intakes (AIs) for Vitamin D

| Age | Children | Men | Women | Pregnancy | Lactation |
|---|---|---|---|---|---|
| Birth to 13 years | 5 mcg (200 IU) | | | | |
| 14-18 years | | 5 mcg (200 IU) | 5 mcg (200 IU) | 5 mcg (200 IU) | 5 mcg (200 IU) |
| 19-50 years | | 5 mcg (200 IU) | 5 mcg (200 IU) | 5 mcg (200 IU) | 5 mcg (200 IU) |
| 51-70 years | | 10 mcg (400 IU) | 10 mcg (400 IU) | | |
| 71+ years | | 15 mcg (600 IU) | 15 mcg (600 IU) | | |

The recommended amount of L-carnitine to be administered is between 400 mg and 3000 mg for adults, and 20 mg and 400 mg for children. Lower amounts may be necessary in preventative cases or premature/neonate cases.

While these ranges may be used as a guide, the best practice is for the physician to determine the amount based upon the age, weight and severity of the condition.

For example: a patient (later referred to as Example 2) suffered cerebrospinal folate deficiency from birth until receiving treatment more than five years after birth. The child was treated with folinic acid at 5 mg twice per day. This dosage was necessary to address the extreme deficiency the child had developed starting in utero. In other cases, especially newborns, who may not have yet manifested any clinical presentations, lower allowances may suffice for prevention purposes.

In another example: a patient (later referred to as Example 1, and also a twin of Example 2) suffered from clinical signs of cerebrospinal folate deficiency at birth. Example 1 received infant milk formula that contained vitamin B12. However, it was not until Example 1 received a separate multivitamin nutritional supplement that contained 2 mcg of vitamin B12 (500% more than the 0.4 mcg NIH recommended daily allowance) that Example 1 showed hematological response. As further addressed in the Examples below, although Example 1 exhibited at birth and in the months thereafter signs of cerebrospinal folate deficiency, over time the damages Example 1 suffered as a result of cerebrospinal folate deficiency were not as severe as Example 2. This is due to Example 1 receiving additional vitamin B12 supplementation after birth and obtaining hematological response.

To the extent that this invention is treating a fetus, a premature newborn or a term neonate who may also be receiving adequate nutritional supplementation from other sources given such individual's then current medical status, trace amounts of folate and B12 can be sufficient to prevent the thyroid-related medical conditions. What is important is to determine the total amounts of these vitamins from all of the mother's nutritional intake in determining the proper amounts to be administered by this embodiment of the invention.

In another embodiment, this invention provides a method to prevent and/or treat harmful conditions that arise from hyperthyroidism. While it is more common that folate deficiencies arise from hypothyroidism, patients with hyperthyroidism are also at risk due to the fact that they are taking drugs that suppress thyroid function. The administration of folate, or reduced folates, and vitamin B12 will help prevent or treat problems in conditions that arise when the thyroid is suppressed to levels that will cause folate deficiency. One of the discoveries of this invention is that there are incidents where people who have been taking anti-thyroid drugs have taken an amount that actually lowered the thyroid function to below normal or that have adversely affected the hematological or hepatic conditions of the patient. A preferred embodiment of the invention prevents and/or treats the complications that arise from such abnormal function. This preferred embodiment would couple treatment of anti-thyroid drugs with the administration of a folate, or a reduced folate, and vitamin B12. In another embodiment, this administration may also be coupled with the administration of iron, L-carnitine, calcium or vitamin D, which may be administered by any manner already known in the art.

In one embodiment, the condition that is a result of improper thyroid function is cerebrospinal folate deficiency. In another embodiment, masked megaloblastic anemia or a masked macrocytic anemia, or a macrocytic anemia is the condition that is a result of improper thyroid function. Both of these conditions have recently been linked to improper thyroid function. The present invention presents methods and compositions to prevent and treat cerebrospinal folate deficiency and masked macrocytic anemias that have arisen in patients with improper thyroid function.

In one embodiment, a folate and vitamin B12 are administered to prevent masked megaloblastic anemia or a masked macrocytic anemia, or a macrocytic anemia in a person that suffers adverse conditions as a result of thyroid-related medical conditions. In cases of masked megaloblastic anemia or masked macrocytic anemia, or a macrocytic anemia this administration may be coupled with the administration of iron. The amount of iron necessary will be dependent upon the amount of iron anemia. It is to be cautioned, that overdoses of iron are also harmful and could interfere with certain thyroid drugs' absorption rates. In another embodiment this administration may also be coupled with the administration of calcium, yet, it should also be noted that calcium may interfere with the absorption rate of certain thyroid drugs. Both the iron and the calcium may be administered by any manner already known in the art. In another embodiment, this administration may also be coupled with the administration of L-carnitine or vitamin D, which may be administered by any manner already known in the art.

In one embodiment, the condition that is a result of a thyroid-related medical condition is hepatic dysfunction. In thyroid-related medical conditions, the hepatic dysfunction can be idiosyncratic or difficult to diagnose given its unpredictability and sudden onset. The liver is one of the major sites for folate and vitamin B12 storage and metabolism. The present invention provides methods and compositions to prevent and treat the adverse effects caused by hepatic dysfunction, by the provision of folate, or a reduced folate, and vitamin B12. In another embodiment, this administration may also be coupled with the administration of iron, L-carnitine, calcium or vitamin D, which may be administered by any manner already known in the art.

Another condition that results in improper thyroid function is hypothyroxinemia or other temporary period of hypothyroidism. Hypothyroxinemia is when a person suffers from an abnormally low concentration of thyroxine in the blood. Hypothyroxinemia has also been discovered to be linked to folate deficiency. In one embodiment of this invention, folate, or reduced folates, and vitamin B12 are administered to a person with hypothyroxinemia to prevent and/or treat complications as a result of hypothyroxinemia. In another embodiment, this administration may also be coupled with the administration of iron, L-carnitine, calcium or vitamin D, which may be administered by any manner already known in the art.

Many times when an individual is treated with radioactive iodine this impairs normal thyroid function. One embodiment of this invention prevents and/or treats complications that arise from treatment with radioactive iodine through the administration of folate, or reduced folates, and vitamin B12. Additionally, persons may undergo surgery on or related to the thyroid gland or have other medical procedures that result in the reduced size or activity of the thyroid. Complications arising from such treatments may be alleviated by the administration of folate, or reduced folates, and vitamin B12. In another embodiment, this administration may also be coupled with the administration of iron, L-carnitine, calcium or vitamin D, which may be administered by any manner already known in the art.

A person who may be taking a thyroid stimulating drug to increase the amount of thyroid hormone may suffer conditions related to the naturally decreased amount of thyroid hormone. In a preferred embodiment of the invention, a folate, or a reduced folate, and vitamin B12 are administered along with the thyroid stimulating drug to a person taking a thyroid stimulating drug. In another embodiment, this administration may also be coupled with the administration of iron, L-carnitine, calcium or vitamin D, which may be administered by any manner already known in the art.

Clinical conditions from abnormal thyroid function in pregnant or nursing women may be passed along to the fetus and/or later newborn. One embodiment of this invention will administer folate, or a reduced folate, and vitamin B12 to these pregnant or nursing women. Some thyroid-related medical conditions prevent absorption and/or reduction of folates in pregnant women. Thus, even though a pregnant woman may be taking a prenatal vitamin supplement that includes a folate (generally folic acid), the thyroid-related medical conditions are preventing the biologically active folates from reaching the fetus. Thus, the fetus then suffers the adverse conditions from the thyroid-related medical condition of the mother. The embodiments of this invention, providing reduced folates to a pregnant woman with thyroid-related medication conditions, will help prevent the fetus from suffering adverse effects by providing the necessary reduced folates for development. In another embodiment, this administration may also be coupled with the administration of iron, L-carnitine, calcium or vitamin D, which may be administered by any manner already known in the art.

Additionally, other thyroid-related medical conditions can cause vitamin B12 deficiencies in pregnant women. Even if the mother is taking a prenatal vitamin with folates and/or vitamin B12, the thyroid-related medical conditions can impair the mother's ability to reduce the folates into its biologically active form. Thus, the newborn suffers adverse conditions. The embodiments of this invention, provide vitamin B12 to a pregnant woman with thyroid-related medication conditions and will help prevent the fetus from adverse effects by providing the necessary vitamin B12 to enable the reduction of folates needed for development. In another embodiment, this administration may also be coupled with the administration of iron, L-carnitine, calcium or vitamin D, which may be administered by any manner already known in the art.

Common treatment for thyroid conditions is the administration of anti-thyroid drugs. An anti-thyroid drug is a hormone antagonist acting upon thyroid hormones. Examples include: propylthiouracil, methimazole, carbimazole, and potassium perchlorate.

Since people taking an anti-thyroid drug are susceptible to developing conditions related to decreased folate levels, one embodiment of this invention provides a composition which comprises an anti-thyroid drug coupled with a folate, or a reduced folate, and vitamin B12. Administration of these nutrients along with the drug would prevent a folate deficiency from arising or treat a folate deficiency.

Propylthiouracil is a common anti-thyroid drug. Propylthiouracil is a thioamide drug used to treat hyperthyroidism (including Graves disease) by decreasing the amount of thyroid hormone produced by the thyroid gland. PTU inhibits the enzyme thyroperoxidase. Propylthiouracil is classified as Drug Class D in pregnancy. Class D signifies that there is positive evidence of human fetal risk. Maternal benefit may outweigh fetal risk in life-threatening situations. The primary effect on the fetus from transplacental passage of PTU is the production of a mild hypothyroidism when the drug is used close to term. This usually resolves within a few days without treatment. The hypothyroid state may be observed as a goiter in the newborn and is the result of increased levels of fetal pituitary thyrotropin. In one embodiment, a composition of propylthiouracil, folate, or a reduced folate, and vitamin B12 is created to be administered to people who need to take anti-thyroid drugs.

Methimazole is another common anti-thyroid drug. In another embodiment, a composition of methimazole, folate, or a reduced folate, and vitamin B12 is created to be administered to people who need to take anti-thyroid drugs.

This invention is not limited to the specific anti-thyroid drugs that are mentioned, rather a composition of any anti-thyroid drug may be coupled with a folate, or reduced folate, and vitamin B12. In another embodiment, this administration may also be coupled with the administration of iron, L-carnitine, calcium or vitamin D, which may be administered by any manner already known in the art.

VI. Treatment Methods

Many embodiments of this invention require the administration of folate, or reduced folates, and vitamin B12. Folates are administered to treat the folate deficiency created by the thyroid-related medical conditions. In one embodiment, folic acid is the folate that is administered with the vitamin B12. Folic acid is not biologically active, but it is an effective treatment for many people who have the ability to convert folic acid into its tetrahydrofolate derivatives.

In some instances folic acid treatment is not enough as folic acid is not the biologically active form of folate. Some individuals have difficulty reducing folic acid into its more biologically active form, therefore, it is necessary to provide these individuals with a reduced folate. A preferred embodiment of the invention is the administration of a reduced folate with vitamin B12.

It is estimated that administration of a reduced folate with vitamin B12 is sufficient to prevent and treat a large percentage of people with thyroid conditions. However, a material percentage must still receive 5-methyltetrahydrofolic acid and vitamin B12 to adequately prevent and/or treat the conditions brought upon by the folate deficiencies due to thyroid-related medical conditions. This is the most preferred embodiment of the invention. Indeed, even if an individual's blood levels of folate are treated and brought to normal, if the degree of folate deficiency was significant or prolonged over a sustained period of time such that the individual's folate stores were depleted, then the cerebrospinal folate levels will remain low despite normalization of folate levels in the blood.

Further, while in some cases the treatment of folate may be enough to treat the folate deficiencies, in other cases the administration of vitamin B12 is essential. Vitamin B12 is essential for folates to become biologically active. It has been observed that one may suffer cerebrospinal folate deficiency and yet have normal folate blood levels. That is because there is folate that is in the blood, however, because of the deficiency in vitamin B12, the folate does not become biologically active.

For example: Example 1 and Example 2 (as discussed below) were born and diagnosed with hypothyroidism. Upon birth, Example 1 presented with more severe clinical conditions than Example 2. However, Example 1 received an additional multivitamin nutritional supplement that included 2 mcg of vitamin B12. Example 2 did not receive the same multivitamin nutritional supplement that included 2 mcg of vitamin B12. Approximately five years after birth, Example 2 was tested for cerebrospinal folate deficiency and was found to be deficient in cerebrospinal folate. Example 1 was tested approximately four months after Example 2's cerebrospinal folate test and was normal in cerebrospinal folate values.

VII. Compositions

One embodiment of the invention includes a composition of an anti-thyroid drug, folate, and vitamin B12. In one embodiment of this invention, this composition would be administered to a pregnant woman with hyperthyroidism. The anti-thyroid drugs could be any drug that has been approved to treat an overactive thyroid gland or suppress thyroid function. A nonexclusive list includes: propylthiouracil, methimazole, carbimazole, and potassium perchlorate. The amounts of anti-thyroid drug would be the amounts a physician would prescribe that is appropriate for the patient's condition. The amount of folate should be at least 30% or more of the generally recommended allowance by the NIH, depending on what additional supplements the patient may be taking. The amount of vitamin B12 should be at least 30% or more of the generally recommended allowance by the NIH, depending on what additional supplements the patient may be taking. Dosage amounts may need to be increased or decreased depending on such factors. For instance, with respect to Example 1 (as discussed above and below), 2 mcg of vitamin B12 per day was required for Example 1 to show hematological improvement, which equates to a 500% increase over NIH's recommended daily allowance. This composition may be administered by any means necessary already known in the art. In a preferred embodiment, the composition would be administered in a capsule containing all three elements. The capsule could be made by any means necessary already known in the art.

The combination of an anti-thyroid drug and folate and vitamin B12 will serve to provide folate and vitamin B12 to the patient and prevent folate deficiencies including cerebrospinal folate deficiency. The vitamin B12 is necessary to help the folate transport into the cerebral spinal fluid.

In a more preferred embodiment of the invention, a composition would include an anti-thyroid drug, a reduced folate, and vitamin B12. The amount of reduced folate should be at least 30% or more of the generally recommended allowance of folic acid by the NIH, depending on what additional supplements the patient may be taking. Dosage amounts may need to be increased or decreased depending on such factors. Since reduced folates are more biologically active, a reduced folate would be more effective in treating folate deficiencies. Additionally, those individuals who reduce folic acid would be benefited by taking a reduced folate. It is estimated that this composition would be effective for a significant percentage of persons with cerebrospinal folate deficiency. For the remaining population, 5-methyltetrahydrofolic acid is necessary.

In a more preferred embodiment of the invention, a composition would include an anti-thyroid drug, 5-methyltetrahydrofolic acid, and vitamin B12. The amount of 5-methyltetrahydrofolic acid should be at least 30% or more of the generally recommended allowance for folic acid by the NIH. In another preferred embodiment, the amount of 5-methyltetrahydrofolic acid should be based on a formula of 0.1-1.0 mg/kg/day. Depending on what additional supplements the patient may be taking, dosage amounts may need to be increased or decreased depending on such factors.

Since other complications arise from thyroid-related medical conditions, another embodiment of this invention includes a composition that includes an anti-thyroid drug, a folate, vitamin B12, and/or iron, and/or L-carnitine and/or calcium and/or vitamin D. L-carnitine has shown to improve mental development in cellular metabolism. These functions are necessary for those susceptible to folate deficiencies. In addition, Example 2 (described below) became hypothyroid as a result of anti-thyroid drug treatment in the mother. At the time Example 2 was diagnosed with cerebrospinal folate deficiency, Example 2 also had a deficiency in L-carnitine. Anti-thyroid drugs have been shown to cause hypothyroidism, and hypothyroidism causes iron deficiencies; therefore, iron supplements may be suitable to correct any iron deficiency. Further, to the extent the hyperthyroidism treatment causes hypothyroidism, hypothyroidism has been found to be associated with hypoparathyroidism. Calcium is effective in the treatment of hypoparathyroidism, and vitamin D assists in the absorption of calcium.

In another embodiment of the invention, a composition would include a thyroid-stimulating drug, folate, and vitamin B12. In one embodiment of this invention, this composition would be administered to an individual with hypothyroidism. The thyroid-stimulating drug could be any drug or hormone that has been approved to treat underactive thyroid function. A nonexclusive list includes: Levothyroxine, Levothyroxine Sodium, Liothyronine Sodium, Liotrix, Thyroglobulin, Thyroid, Thyroxine, Triiodothyronine, Levoxyl, Synthroid, Levo-T, Unithroid, Levothroid, Levoxine, Levolet, Novothyrox, Triostat, Cytomel and Thyrolar. The amounts of thyroid-stimulating drug would be the amounts a physician would prescribe that is appropriate for the patient's condition. The amount of folate should be at least 30% or more of the generally recommended allowance by the NIH, depending on what additional supplements the patient may be taking. The amount of vitamin B12 should be at least 30% or more of the generally recommended allowance by the NIH, depending on what additional supplements the patient may be taking. Dosage amounts may need to be increased or decreased depending on such factors. For instance, with respect to Example 1 (as discussed above and below), 2 mcg of vitamin B12 per day was required for Example 1 to show hematological improvement, which equates to a 500% increase over NIH's recommended daily allowance. This composition may be administered by any means necessary already known in the art. In a preferred embodiment, the composition would be administered in a capsule containing all three elements. The capsule could be made by any means necessary already known in the art.

The combination of a thyroid-stimulating drug and folate and vitamin B12 will serve to provide folate and vitamin B12 to the patient and prevent folate deficiencies including cerebrospinal folate deficiency. The vitamin B12 is necessary to help the folate transport into the cerebral spinal fluid.

In a more preferred embodiment of the invention, a composition would include a thyroid-stimulating drug, a reduced folate, and vitamin B12. The amount of reduced folate should be at least 30% or more of the generally recommended allowance of folic acid by the NIH, depending on what additional supplements the patient may be taking. Dosage amounts may need to be increased or decreased depending on such factors. Since reduced folates are more biologically active, a reduced folate would be more effective in treating folate deficiencies. Additionally, those individuals who reduce folic acid would be benefited by taking a reduced folate. It is estimated that this composition would be effective for a significant percentage of persons with cerebrospinal folate deficiency. For the remaining population, 5-methyltetrahydrofolic acid is necessary.

In a more preferred embodiment of the invention, a composition would include a thyroid-stimulating drug, 5-methyltetrahydrofolic acid, and vitamin B12. The amount of 5-methyltetrahydrofolic acid should be at least 30% or more of the generally recommended allowance for folic acid by the NIH. In another embodiment, the amount of 5-methyltetrahydrofolic acid should be based on a formula of 0.1-1.0 mg/kg/day. Depending on what additional supplements the patient may be taking, dosage amounts may need to be increased or decreased depending on such factors.

Since other complications arise from thyroid-related medical conditions, another embodiment of this invention includes a composition that includes a thyroid stimulating drug, a folate, vitamin B12, and/or iron, and/or L-carnitine and/or calcium and/or vitamin D. L-carnitine has shown to improve mental development in cellular metabolism. These functions are necessary for those susceptible to folate deficiencies. In addition, Example 2 (described below) became hypothyroid as a result of anti-thyroid drug treatment in the mother. At the time Example 2 was diagnosed with cerebrospinal folate deficiency, Example 2 also had a deficiency in L-carnitine. Hypothyroidism causes iron deficiencies; therefore, iron supplements may be suitable to correct any iron deficiency. Further, hypothyroidism has been found to be associated with hypoparathyroidism. Calcium is effective in the treatment of hypoparathyroidism, and vitamin D assists in the absorption of calcium.

VIII. Examples

The following examples illustrate the medical conditions presented in twins who were born to a mother diagnosed with hyperthyroidism who had excessive anti-thyroid drug treatment during the pregnancy that, as a result, created a hypothyroid state in the mother as well as a hypothyroid state in the twin neonates.

Example 1 and Example 2 were both infant patients.

Both Example 1 and Example 2 were born to a mother who was diagnosed with hyperthyroidism and was treated with excessive anti-thyroid drugs during the pregnancy, thus creating a hypothyroid state in the mother, and in the fetuses. It was later determined that both Example 1 and Example 2 were hypothyroid in utero.

Both Examples 1 and 2 received thyroid stimulating drugs after birth and became euthyroid within approximately one week of birth.

Immediately after birth, Example 1 had evidence of megaloblastic anemia and neutropenia. Example 2 had evidence of masked megaloblastic anemia, as well as neutropenia that may have been masked. It is notable that Example 2's hematological testing was performed approximately one hour after Example 1's hematological testing, a period of time in which neutrophil and white blood cell values have been shown to rise. Both Example 1 and Example 2 showed signs of hepatic dysfunction. It is notable that the mother showed signs of idiosyncratic hepatic dysfunction during the pregnancy while taking anti-thyroid drugs.

Both Example 1 and Example 2 were treated for iron deficiencies with iron supplements.

Example 1 and Example 2 received different nutritional supplementation with respect to vitamin B12. Although Example 2 did receive the same infant milk formula that Example 1 received, which infant milk formula contained vitamin B12, Example 2 received less of the infant milk formula than Example 1, and Example 2 received in lieu of the infant milk formula more of the breast milk from the hypothyroid mother. Example 1 also received an additional multivitamin nutritional supplement that included 2 mcg of vitamin B12. Example 2 received a different version of the multivitamin nutritional supplement that did not include vitamin B12.

When Example 1 received the additional nutritional supplement containing 2 mcg of vitamin B12, Example 1 showed prompt hematological response by an increase in reticulocytes, moving from below normal to normal, which is evidence of a treated vitamin B12 and/or folate deficiency. Example 2, however, showed regression in reticulocyte values and remained below normal, evidencing a continued vitamin B12 and/or folate deficiency.

Both Example 1 and Example 2 exhibited signs associated with cerebrospinal folate deficiency at birth and within the ensuing year, including, but not limited to, failure to thrive, drowsiness, pallor, glossitis, sepsis and septicemia, as well as neurological manifestations including cognitive impairment, movement disorders and peripheral neuropathy. For the most part, Example 2 exhibited more drastic versions of the symptoms, including behavioral and social issues and painful movement disorders.

In summary, it has been determined that the proper maternal folate metabolism, which was altered by the excessive anti-thyroid drug treatment, the mother's hypothyroidism, and pernicious anemia, critically affected delivery of folate to the embryo and transport of intact folate across the placenta. This means that Example 1 and Example 2 began to suffer from systemic folate deficiency in the womb, and systemic folate deficiency leads to cerebrospinal folate deficiency. Example 1's and Example 2's folate condition was also impacted by their own hypothyroidism and placental transfer of the mother's anti-thyroid drug. It is notable that the thyroid stimulating drugs that Example 1 and Example 2 received immediately after birth and which brought each of them to a euthyroid state within approximately a week did not sufficiently address cerebrospinal folate deficiencies, nor was the prompt hematological response seen in Example 1 after additional vitamin B12 supplementation associated with the thyroid stimulating drugs treatment.

Both Example 1 and Example 2 displayed a number of conditions consistent with cerebrospinal folate deficiency. Example 1 and Example 2 are similar in that both Example 1 and Example 2 had a mother treated with an anti-thyroid drug and that was diagnosed with hypothyroidism, thereby resulting in hypothyroidism in Example 1 and Example 2. Additionally, both Example 1 and Example 2 had goiters at birth, had similar lab treatment in the hospital after birth, and lived a somewhat similar life (food, upbringing, school, same medications and vitamin supplements, vaccinations, etc.) after discharge from the hospital. One significant difference was that Example 1 received more vitamin B12 supplementation than Example 2, and Example 1 showed prompt hematological response.

The Importance of Reduced Folates, Especially 5-Methyltetrahydrofolate or Folinic Acid Although Example 1 suffered and continues to suffer from symptoms associated with the onset of cerebrospinal folate deficiency, Example 1's manifestations have been to a lesser degree than Example 2. Example 2 has suffered, and continues to suffer, from symptoms of cerebrospinal folate deficiency to a greater degree than Example 1.

Approximately five years and three months after birth, cerebospinal folate levels were observed for the first time in Example 2. Example 1 was tested for cerebrospinal folate deficiency approximately four months after Example 2's testing. Example 1 showed normal levels of cerebrospinal folate, which is consistent with the additional vitamin B12 support Example 1 received after birth (and the resulting hematological response), and the lesser degree of symptoms associated with the onset of cerebrospinal folate deficiency that Example 1 has suffered from. Studies have shown that the earlier the anemias associated with cerebrospinal folate deficiency are addressed, the better the adversely impacted individual can overcome more long-term effects of the associated folate deficiency. Notwithstanding Example 1's cerebrospinal folate deficiency test results, Example 1 still has permanent neurological damage resulting from cerebrospinal folate deficiency at birth, demonstrating the need for the methods and compositions of this invention.

Example 2 showed below normal levels of cerebrospinal folate, which is consistent with Example 2'slack of hematological response after birth given Example 2's lesser vitamin B12 supplementation, and the higher degree of symptoms associated with cerebrospinal folate deficiency that Example 2 has suffered from. After Example 2's diagnosis, Example 2 was placed on 5-methyltetrahydrofolate in the form of folinic acid (5 mg twice per day). Within approximately four months, Example 2's cerebrospinal folate levels rose from 32 L (preferred range 40-128) to approximately 88 (middle of the range). Thus after four months of treatment, Example 2 achieved normal cerebrospinal folate levels, while Example 2 could not achieve such normal levels within the first five years of Example 2's life even when receiving multivitamins with folic acid and vitamin B12. Thus, reduced folates are critical.

After 5-methyltetrahydrofolate treatment, Example 2 showed improvement in physical, behavioral and social skills.

I claim:

1. A composition, comprising: (a) a drug, agent, or medication that acts as a replacement for a hormone that is normally produced by the thyroid gland selected from the group consisting of levothyroxine, levothyroxine sodium, liothyronine sodium, liotrix, thyroxine and triiodothyronine, and (b) a reduced folate selected from the group consisting of 5-methyltetrahydrofolic acid and 6(S)-5-methyltetrahydrofolate.

2. The composition of claim 1, wherein the reduced folate itself does not contain calcium.

3. The composition of claim 1, wherein the reduced folate is 5-methyltetrahydrofolic acid and the 5-methyltetrahydrofolic acid itself does not contain calcium.

4. The composition of claim 1, wherein the reduced folate is 6(S)-5-methyltetrahydrofolate and the 6(S)-5-methyltetrahydrofolate itself does not contain calcium.

* * * * *